United States Patent [19]
McLees

[11] Patent Number: 5,496,325
[45] Date of Patent: Mar. 5, 1996

[54] SPLIT STEM SURGICAL SAW BLADE

[76] Inventor: Donald J. McLees, 2623 Virginia Ave., Everett, Wash. 98201

[21] Appl. No.: 287,933

[22] Filed: Aug. 9, 1994

[51] Int. Cl.⁶ ........................................ A61B 17/14
[52] U.S. Cl. .................. 606/82; 606/178; 30/316; 30/334; 30/342
[58] Field of Search .................. 606/82, 178, 179, 606/177, 176, 79; 30/166.3, 380, 502, 514, 517, 356, 316, 334, 342

[56] References Cited

U.S. PATENT DOCUMENTS

| | | | |
|---|---|---|---|
| 2,019,009 | 10/1935 | Hendrix | 30/316 |
| 4,402,137 | 9/1983 | Kovach | 30/316 |
| 5,092,875 | 3/1992 | McLees | 606/82 |
| 5,103,563 | 4/1992 | Johnson | 30/316 |

*Primary Examiner*—Tamara L. Graysay

[57] ABSTRACT

A bone plug cutting blade for a peripheral drive oscillating surgical saw. The blade has a split stem so that it can be placed around a tendon attached to the bone before being inserted into the saw's blade holder.

5 Claims, 1 Drawing Sheet

SPLIT STEM SURGICAL SAW BLADE

BACKGROUND OF THE INVENTION

1. Field of the Invention

This invention relates in general to surgery and specifically to bone-tendon-bone graft harvesting for knee ligament reconstruction. It would be found in the patent files in a classification for surgical bone cutting implements.

2. Prior Art

There has long been a need for a more efficient means of harvesting the graft for ACL reconstruction of the knee. In such surgery a graft consisting of a portion of tibia bone, a portion of patella tendon and another bone portion from the patella is removed from the knee of the patient and arthroscopically relocated inside the knee to replace a damaged anterior cruciate ligament (ACL). Historically the preferred method of bone portion removal has been with osteotomes (chisels), leaving irregular pieces of bone which then have to be trimmed and sized by hand to the approximate shape of cylinders for fitting into the drilled out tibial and femoral tunnels inside the knee.

In order to more efficiently harvest the graft, introduce less trauma at the donor site and provide for a better bone plug/drilled tunnel fit, the ACL bone saw was developed (U.S. Pat. No. 5,092,875). The ACL bone saw peripherally oscillates a ring of teeth about its center by means of an attached drive arm. Thus the ACL saw is substantially different from a standard plug cutter in that it has no shaft and therefore can easily be inserted into pre-cut notches in the tibia and patella for removal of cylindrical bone plugs.

A device from Australia called the Helical Tube Saw has also been developed to harvest the graft. It appears much the same as a standard plug cutter with the exception of an additional helical slot open ended at the teeth and running longitudinally along the tube. Such a configuration allows the cutting tube to wrap around the tendon portion of the graft as it cuts the bone portion from the proximal end (tendon end first) with the knee flexed to 90 degrees. The device must be oscillated by hand and the complexity of the blade hinders its use as a one-time only disposable item.

However, from a physician's standpoint, it is desirable to initiate the bone cut from the tendon end rather than the distal bone plug end. Also, if the ACL bone saw could be made to cut in that direction, it would further reduce trauma at the donor site by eliminating the need for pre-cut blade insertion notches.

SUMMARY OF THE INVENTION

In order to satisfy the objective of allowing the ACL bone saw to harvest the graft by cutting the bone portions from the tendon end first, the split stem blade was conceived. A further object of the invention is to provide a one-time use blade that is easy to fabricate. A still further object is to provide such a blade which is simple to use in that it can be easily inserted into the blade holder, positively locked, and then easily removed without the need for additional tools.

The split stem blade satisfies all the objectives of the invention. Instead of having a closed ring of teeth, the split stem blade has an open teeth ring with two stems, one on each side of the opening. During the ACL reconstruction procedure the split stem concept allows the surgeon to slip the open blade around the graft tendon portion, close the blade and push the stems into the blade holder. The first bone portion can then be cut, its end separated by an osteotome and that portion of the graft pulled back through the saw blade. The saw can then be turned around, the graft slipped back through the blade and the second bone portion can then be removed by the same process.

DETAILED DESCRIPTION

Figure 1:
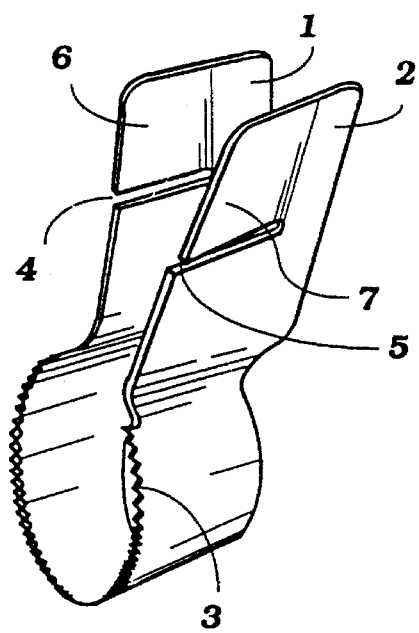
FIG. 1 is a front view isometric drawing showing the entire blade.
Figure 2:
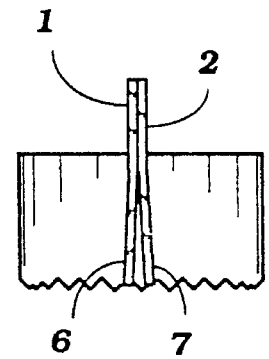
FIG. 2 is a top view showing the blade in its closed position.
Figure 3:
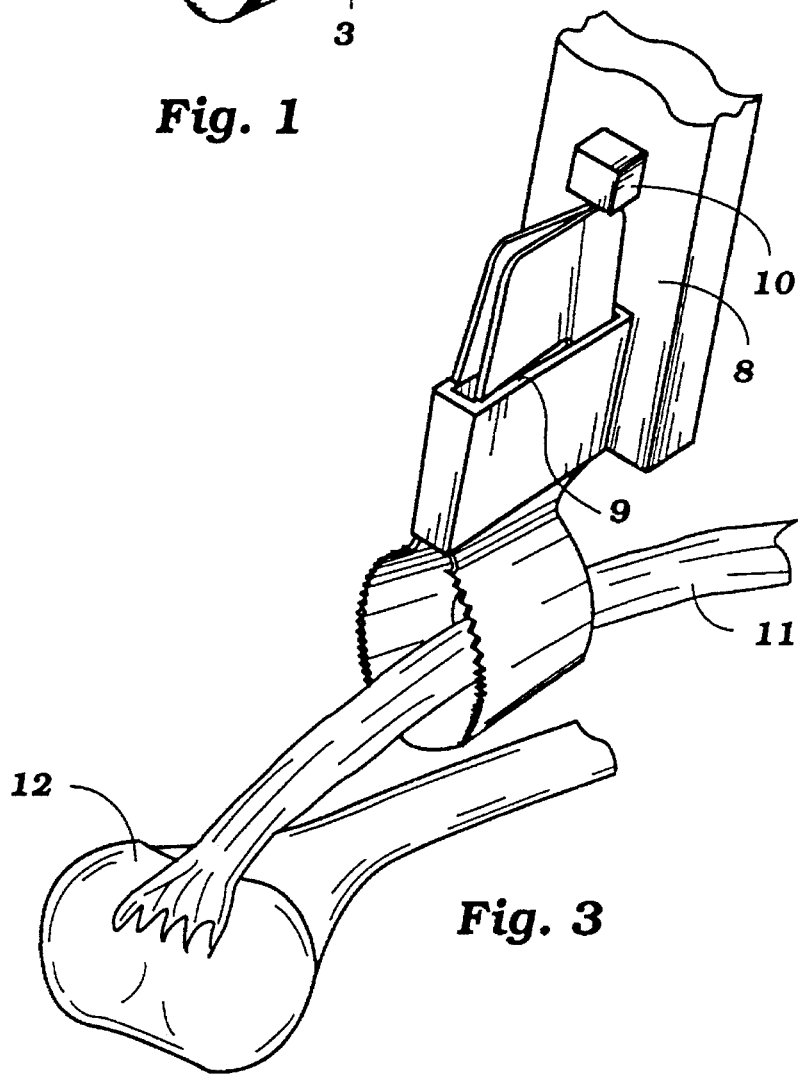
FIG. 3 is a front view isometric drawing showing the blade in its holder with a tendon passing through the blade and attached to a bone.

The blade as shown in its open configuration in FIG. 1 has two slotted stems 1 and 2. When squeezed together the two stems form a single split blade stem and the toothed portion becomes a circular ring 3 having an inside diameter of either 8, 9, 10 or 11 mm. to accomodate different sized patients. The split stem configuration is actually easier to fabricate than a closed ring with a stem attached. The stems are tapered slightly so as to be easily inserted into the blade holder and they are also bent outward slightly at the slots 4 and 5 to form tabs 6 and 7 as shown in FIG. 2. Insertion of the blade into the holder 8 of FIG. 3 causes the tabs to be pushed back together until they pass the lower stop 9 of the holder, at which point the tabs are allowed to snap apart and thereby prevent the blade from moving downward while the top of the blade stem contacts the holder's upper stop 10 and thereby prevents the blade from moving upward. Thus the blade's own spring force is used to lock the blade into place. To remove the blade the tabs are simply squeezed together and the blade pulled out. FIG. 3 shows a tendon portion 11 passing through the blade and attached to the bone 12 from which the bone plug is to be cut.

Figure 4:
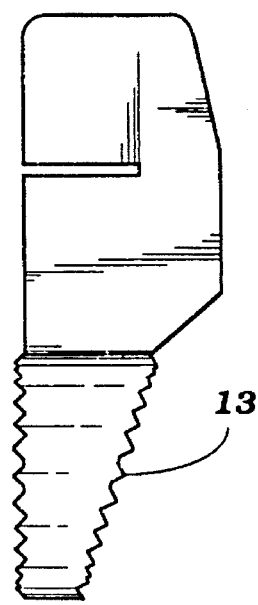
FIG. 4 is a side view of a self-entering version of the blade.

FIG. 4 illustrates an alternative version of the blade which includes a tapered teeth ring with a second set of teeth 13 around the back of the blade. By tilting this blade forward and back while cutting forward and back the surgeon can cause the blade to self-enter or self-exit the bone, thereby eliminating the need for an osteotome to separate the bone plugs at their ends.

What is claimed is:

1. A peripherally driven bone cutting surgical blade in operative combination with an oscillating drive mechanism, said blade comprising an open ring with teeth protruding from a leading edge and peripheral drive attachment means, said open ring of teeth being closeable to form a substantially circular teeth ring, and said oscillating drive mechanism causing the blade to oscillate about a central longitudinal axis of the teeth ring.

2. The blade of claim 1 in which the peripheral drive attachment means is provided by two stems, one of said stems being an extension of the ring on one side of the ring opening and the other of said stems being an extension of the ring on the other side of the ring opening, and both of said stems extending substantially outward radially from the center of the ring.

3. The blade of claim 1 also having teeth protruding from a trailing edge of the ring.

4. A peripherally driven bone cutting surgical blade and blade holder in operative combination with an oscillating drive mechanism comprising:

an open ring with teeth protruding from a leading edge, said ring having two stems, one of said stems being an extension of the ring on one side of the ring opening and the other of said stems being an extension of the ring on the other side of the ring opening, both of said stems extending substantially outward radially from the center of the ring, said ring and said stems being closeable to form a substantially circular teeth ring with said stems being in contact with each other, and a holder for said stems, said holder and said stems in combination having locking means whereby said stems and said holder can be firmly locked together, and an oscillating drive mechanism attached to the holder, said oscillating drive mechanism causing the holder and blade to oscillate about a central longitudinal axis of the teeth ring.

5. The blade and blade holder of claim 4 with the locking means being provided by said holder in communication with the stems, each of said stems having a tab, said tabs being a portion of each stem distal of an open ended slot through each stem, said slots being substantially parallel to the central longitudinal axis of the teeth ring and extending partially across each stem, said tabs being bent outward slightly from a centerline between the two stems, said holder having a top member preventing said stems from moving upward, a front member preventing said stems from moving forward, a rear member preventing said stems from moving rearward, a left side member preventing said stems from moving to the left, and a right side member preventing said stems from moving to the right, each side member having an upper surface preventing said bent tabs from moving downward, said blade being releaseable from said blade holder by compression of said bent tabs toward the centerline between the stems.

* * * * *